United States Patent [19]
Huffman et al.

[11] 4,299,969
[45] Nov. 10, 1981

[54] METHOD FOR PREPARING LOWER ALKYL β-(S-BENZYLMERCAPTO)-β,β-PENTAMETHYLENEPROPIONATES

[75] Inventors: William F. Huffman, Malvern; Nelson C. Yim, Ambler, both of Pa.

[73] Assignee: SmithKline Corporation, Philadelphia, Pa.

[21] Appl. No.: 176,372

[22] Filed: Aug. 8, 1980

[51] Int. Cl.³ .......................................... C07C 149/40
[52] U.S. Cl. ....................................................... 560/9
[58] Field of Search ............................................ 560/9

[56] References Cited
PUBLICATIONS
Nestor, J. Med. Chem., 18, pp. 284–287 (1975).

*Primary Examiner*—Natalie Trousof
*Assistant Examiner*—Michael Shippen
*Attorney, Agent, or Firm*—William H. Edgerton; Richard D. Foggio; Alan D. Lourie

[57] ABSTRACT

Lower alkyl β-(S-benzylmercapto)-β,β-pentamethylenepropionates are prepared in improved yields by reacting lower alkyl cyclohexylideneacetates with benzylmercaptan in the presence of an alkali metal mercaptide.

5 Claims, No Drawings

METHOD FOR PREPARING LOWER ALKYL β-(S-BENZYLMERCAPTO)-β,β-PENTAMETHYLENEPROPIONATES

This invention concerns an improvement in the method of preparing the ester precursors of β-(S-benzylmercapto)-β,β-pentamethylenepropionic acid which is an important intermediate for preparing new biologically active polypeptides.

DESCRIPTION OF THE PRIOR ART

Ethyl β-(S-benzylmercapto)-β,β-pentamethylenepropionate is reported by V. duVigneaud et al., J. Med. Chem. 18 284 (1975) to have been prepared by a Michael addition of benzyl mercaptan to ethyl cyclohexylideneacetate in benzene in the presence of boron trifluoride etherate. This reference reports no yield on the Michael addition but an overall crude yield of 17% after hydrolysis to give the desired acid. In our hands an overall yield of about 4% was obtained. The method of the present invention has been unexpectedly found to give much higher yields of the desired ester and acid.

DESCRIPTION OF THE INVENTION

β-(S-Benxylmercapto)-β,β-pentamethylenepropionic acid has been reported to be a precursor in the preparation of vasopressin, a polypeptide compound having biological activity, M. Manning et al., J. Med. Chem. 21 313 (1978) also W. H. Sawyer et al., Mol. Pharmacol. 14 1006 (1978).

The improvement of this invention comprises running the reaction of benzylmercaptan and a lower alkyl cyclohexylideneacetate in the presence of a catalytic quantity of an alkali metal benzylmercaptide, most conveniently sodium or potassium benzylmercaptide. Converting all the benzylmercaptan to alkali metal benzylmercaptide gives little product. The reaction of the prior art used an excess of an acidic reactant, boron trifluoride.

The quantity of the catalytic mercaptide in the claimed reaction is generally from 5–30%, especially about 25%, by weight of the mercaptan starting material. Usually the catalytic quantity of mercaptide is generated from the one mole equivalent of benzylmercaptan starting material. The reaction is carried out in an organic solvent in which the reactants are soluble and to which they are chemically inert. Most useful are benzenoid solvents especially toluene, benzene or xylene combined with an amide solvent such as dimethylformamide or dimethylacetamide. Toluene-dimethylformamide is a convenient solvent system. The reaction is run using substantially stoichiometric quantities of the starting materials in the solvent at temperatures from ambient up to the boiling point until reaction is complete usually from about 1 to 18 hours depending on the temperature of the reaction.

Most conveniently as noted above the mercaptide is prepared by merely adding an alkali metal hydride to the benzyl mercaptan solution prior to reaction with the cyclohexylidene.

When the reaction is complete as indicated by thin layer chromatography, the product is isolated by quenching in water and extraction. Yields of 2–6 times those reported in the prior art are obtained.

The desired β-(S-benzylmercapto)-β,β-pentamethylenepropionic acid is then prepared by standard ester hydrolysis, such as in mild alcoholic alkali, in high yield.

It will be appreciated that any commercially feasible alcohol can be used to esterify cyclohexylideneacetic acid to prepare the ester starting material since the protective group is removed after the Michael reaction. Lower alkyl of 1–6 carbons or benzyl esters can be used but in practice methyl or ethyl cyclohexylideneacetates are the most useful starting materials.

The following example is designed to illustrate the specific practice of this invention but is not intended to limit its scope.

EXAMPLE 1

A mixture of 220 ml of toluene and 7.44 g (7 ml, 0.06 m) of benzylmercaptan is stirred under argon while 720 mg of sodium hydride (59% oil dispersion, ~0.015 m) was added. Dried dimethylformamide was added dropwise until the evolution of gas stopped (~12 ml) and a solution resulted. At that point 10 g (0.06 m) of ethyl cyclohexylideneacetate was added. After stirring briefly the mixture was stoppered and allowed to stand at room temperature for 18 hours.

After analysis by thin layer chromatography (silica; cyclohexane:ethylacetate 95:5), the reaction mixture was poured into 250 ml of ice-water and the mixture extracted with ethyl ether. The combined extracts were dried and evaporated to give 14.7 g (83.7%) of ethyl β-(S-benzylmercapto)-β,β-pentamethylenepropionate acid.

If desired, this product may be purified in high yield by column chromatography over silica with elution using 5% ethyl acetate in cyclohexane.

The ester (4.85 g, 0.0165 m) in a solution of 17 g of anhydrous potassium carbonate and 120 ml of 25% aqueous methanol is heated at reflux for 18 hours. The alcohol is taken off under reduced pressure. The residue is diluted with 200 ml of ice-water. The mixture is washed twice with ether, acidified with hydrochloric acid and extracted with ether. The extracts are dried and evaporated to give 4.1 g of β-(S-benzylmercapto)-β,β-pentamethylenepropionic acid.

Replacing sodium hydride by potassium hydride gives equivalent results.

What is claimed is:

1. In the process of preparing a lower alkyl β-(S-benzylmercapto)-β,β-pentamethylenepropionate by reacting benzyl mercaptide with a lower alkyl cyclohexylideneacetate in an inert organic solvent, the improvement comprising running the reaction in the presence of a catalytic quantity of an alkali metal benzylmercaptide.

2. The process of claim 1 in which the alkali metal benzylmercaptide is sodium or potassium benzyl mercaptide.

3. The method of claim 1 in which the lower alkyl cyclohexylidene acetate is ethyl or methyl cyclohexylideneacetate.

4. The method of claim 1 in which from 5–30% by stoichiometric weight of sodium or potassium benzylmercaptide is used.

5. The method of claims 1, 2, 3 or 4 in which the alkali metal benzylmercaptide is sodium benzylmercaptide, the lower alkyl cyclohexylideneacetate is ethyl cyclohexylideneacetate and the solvent is dimethylformamide.

* * * * *

UNITED STATES PATENT AND TRADEMARK OFFICE
CERTIFICATE OF CORRECTION

PATENT NO. : 4,299,969
DATED : November 10, 1981
INVENTOR(S) : William F. Huffman and Nelson C. Yim It is certified that error appears in the above-identified patent and that said Letters Patent are hereby corrected as shown below:

Column 1, line 26, "Benxylmercapto" should read
-- Benzylmercapto -- .

Column 1, line 28, after the word "of" insert -- [1-(β-mercapto-β,β-cyclopentamethylenepropionic acid), 4-valine, 8-D-arginine] -- .

Signed and Sealed this

Sixteenth Day of March 1982

[SEAL]

Attest:

GERALD J. MOSSINGHOFF

Attesting Officer

Commissioner of Patents and Trademarks